United States Patent
Fodgaard

(10) Patent No.: US 6,943,883 B2
(45) Date of Patent: Sep. 13, 2005

(54) APPARATUS, SAMPLE CUVETTE AND METHOD FOR OPTICAL MEASUREMENTS

(75) Inventor: Henrik Fodgaard, Valby (DK)

(73) Assignee: Radiometer Medical A/S, Bronshoj (DK)

( * ) Notice: Subject to any disclaimer, the term of this patent is extended or adjusted under 35 U.S.C. 154(b) by 165 days.

(21) Appl. No.: 10/198,400

(22) Filed: Jul. 18, 2002

(65) Prior Publication Data

US 2002/0176068 A1 Nov. 28, 2002

Related U.S. Application Data

(63) Continuation of application No. PCT/DK01/00030, filed on Jan. 16, 2001.

(30) Foreign Application Priority Data

Jan. 18, 2000 (DK) .......................................... 2000 00080

(51) Int. Cl.[7] .......................... G01N 21/00; G01N 33/48
(52) U.S. Cl. .......................... 356/436; 356/440; 356/39
(58) Field of Search .................. 356/39, 440, 436–437, 356/246; 422/58, 68.1, 105; 436/66, 70, 165–166

(56) References Cited

U.S. PATENT DOCUMENTS

| | | | |
|---|---|---|---|
| 4,298,275 A | 11/1981 | Critchlow et al. | |
| 4,303,336 A | 12/1981 | Cullis | |
| 4,906,081 A | 3/1990 | Yasuda | |
| 5,088,493 A | 2/1992 | Giannini et al. | |
| 5,104,221 A | * 4/1992 | Bott et al. .................. | 356/336 |
| 5,385,539 A | 1/1995 | Maynard | |
| 5,478,750 A | 12/1995 | Bernstein et al. | |
| 5,601,080 A | 2/1997 | Oppenheimer | |
| 5,750,994 A | * 5/1998 | Schlager ................ | 250/339.11 |
| 5,784,158 A | * 7/1998 | Stanco et al. ............... | 356/326 |
| 5,963,335 A | 10/1999 | Boutelle | |

FOREIGN PATENT DOCUMENTS

| | | |
|---|---|---|
| EP | 0 210 417 B1 | 9/1990 |
| EP | 0 503 874 A2 | 9/1992 |
| EP | 0 575 712 A2 | 12/1993 |
| EP | 0 800 074 A1 | 3/1997 |
| WO | WO 94/08237 | 9/1992 |
| WO | WO 96/37767 | 5/1995 |

OTHER PUBLICATIONS

Record from Derwent's World Patents Index, re: JP 10132728.
Record from Derwent's World Patents, Index re JP19132728.

* cited by examiner

Primary Examiner—Zandra V. Smith
(74) Attorney, Agent, or Firm—Bryan Cave LLP

(57) ABSTRACT

An apparatus, a sample cuvette and a method for optical measurements on samples which show variable levels of scattering are provided. The apparatus, sample cuvette and method may be used for optical measurements on biological, physiological and chemical samples, however, are especially applicable for optical measurements on whole blood.

40 Claims, 5 Drawing Sheets

APPARATUS, SAMPLE CUVETTE AND METHOD FOR OPTICAL MEASUREMENTS

This application is a continuation of PCT/DK01/00030, filed Jan. 16, 2001.

This invention relates to an apparatus, a sample cuvette and a method for optical measurements on samples which show variable level of scattering, in particular to an apparatus, a sample cuvette and a method for optical measurements on samples of whole blood.

Optical measurements in which the transmission of light from a light source across a sample is determined by a detector is a strong tool for a wide range of chemical and clinical investigations. For ideal samples the absorbance is proportional to the concentration of absorbing species in the sample as well as to the sample thickness. Lambert-Beer's law describes this relation according to which:

$$A = \log I_0/I = \epsilon c d,$$

where $I_0$ and $I$ are the intensities of the incident and transmitted light, respectively, c is the concentration of the absorbing species, d is the sample thickness and $\epsilon$ is the extinction coefficient. The term $\log I_0/I$ is referred to as the absorbance A.

For most real samples, however, scattering occurs. Accordingly, the transmission of light is disturbed in a number of ways which complicates measurements and which should be corrected for in order to obtain correct values for those concentrations and parameters sought.

One major reason for scattering is sample inhomogenity, as the light is scattered upon interaction with the particles of inhomogeneous samples. Accordingly, the light is not transmitted directly but deflected over a range of scattering angles. Scattering and scattered light has a circular symmetry and may be characterised by the scattering angle $\alpha$.

The scattering angle $\alpha$ is defined as the angular deviation of scattered light from the central optical path of the light, the vertex of the scattering angle being defined as the center of the sample chamber. The angle of incidence $\beta$ for light reaching the detector is defined as the angle between the incident light and the detector surface. The scattering angle $\alpha$ and the angle of incidence $\beta$ are related as $\alpha+\beta=90°$ for light scattered in the angular range 0–90°.

A number of phenomena related to scattering complicates optical measurements. Thus, scattering of light at angles $\alpha$ outside the detection range of the detector makes this part of the light unavailable for detection. Further, most detectors have a reduced sensitivity to light of low angle of incidence compared to the sensitivity to light of an angle of incidence $\beta=90°$.

Reflection is another phenomenon which should be considered. Reflection of light may occur at any optical interface in the light path. Light scattered to high scattering angles will tend to show higher reflection compared to unscattered light or light scattered to low scattering angels. Finally, scattering causes an increase in the effective optical pathlength and thus the absorbance compared to unscattered light.

The scattering coefficient is defined as the distribution of light intensity vs. scattering angle. Thus, those measurements dominated by massive scattering have high scattering coefficients, whereas measurements of little scattering have low coefficients.

In the case of a fixed scattering coefficient, the above phenomena may easily be corrected for in the data processing step of the measurement. Regrettably, however, the coefficient is not fixed but varies with a range of sample parameters.

The phenomenon of varying scattering coefficients complicates measurements further. Thus, measurements which suffer from scattering beyond the detector range erroneously indicate too high concentrations of absorbing species. There is, however, no immediate way of determining the level of undetected light.

Those measurements of high scattering coefficients have high levels of light of low angle of incidence. Due to reduced sensitivity under such conditions the detector will erroneously indicate too high absorption and too high concentration of absorbing species. As the scattering coefficient, however, varies from to sample to sample, the phenomenon can not be immediately corrected for in the data processing step.

At variable scattering coefficient the level of reflection varies as well. In the case of high reflection, which is predominant at high scattering coefficients, loss of light will be massive and high concentrations of absorbing species will erroneously appear. As above there is no immediate way of determining the loss due to reflection.

The variation of the scattering coefficient also influences the absorbance as ascribed to variations in effective optical pathlength. Those samples which have high scattering coefficients will erroneously appear to have high concentrations of absorbing species, although the increased absorption is in fact due to an increased effective optical pathlength. The effective pathlength varies from sample to sample and cannot be immediately determined.

An important example of such samples which suffer from variable scattering coefficient is whole blood, i.e. blood which has not been hemolysed and which therefore is highly inhomogeneous.

In whole blood, parameters and components traditionally measured by optical methods are the total hemoglobin concentration (tHb), the hematocrit value (HCT), i.e. the fraction of red cell volume relative to total blood volume and the glucose concentration. Specific hemoglobin derivatives like oxyhemoglobin, deoxyhemoglobin, methemoglobin, carboxyhemoglobin and sulfhemoglobin along with bilirubin and diagnostic dyes are examples of other species which may be measured using the optical principles.

In whole blood the concentration, osmotic volumetric variations, aggregation and shaping of blood cells are all parameters which influence the scattering coefficient.

In terms of concentration of blood cells maximum scattering is observed for those samples which have an HCT in the typical range 40–50%. Those samples of higher or lower HCT have lower scattering coefficients.

The scattering coefficient also depends on the mean cell hemoglobin concentration (MCHC) which is defined as the ratio between tHb and HCT (MCHC=tHb/HCT). MCHC is thus the concentration of hemoglobin in the blood cells and is a key parameter in the understanding of the blood cell osmotic volumetric changes.

Osmotic volumetric changes, as caused by variations in the electrolyte concentration, influence the scattering coefficient. At high concentrations, e.g. high concentrations of salts, osmosis causes a flow of water from the blood cells to the plasma phase during which the blood cells are contracted and scattering increased. Thus, although two blood samples have similar hemoglobin concentrations the sample of higher blood cell contraction—and thus higher MCHC—appears to have a higher hemoglobin concentration.

It has been observed that at a given tHb the error on the experimental determination of tHb varies with MCHC. Thus, at a typical level of tHb of 15 g/dl, the experimentally determined tHb may vary by approx. ±4% upon a variation of ±10% of the MCHC. At larger variations of MCHC, e.g. in the range ±25%, the experimentally determined tHb may vary as much as approx. ±13% which is unacceptable for clinical purposes, cf. Example 1 and Comparative Example 1.

Blood cell aggregation, precipitation and abnormal shaping as observed in the case of sickle cell disease are other phenomena which influence the scattering coefficient. Thus, upon aggregation and precipitation, the coefficient decreases, indicating erroneously a too low concentration of hemoglobin compared to unprecipitated samples. Abnormal shaping as well may lead to changes of the scattering coefficient.

As the level of scattering is further influenced by the concentrations of specific lipids and proteins the complete phenomenon of scattering and the variable level thereof is highly complex. Accordingly, a high number of patents has dealt with the problem of measuring blood parameters by optical methods, i.e. photometric and spectroscopic methods. Those patents may merely be divided into two groups, the first group pursuing geometrical solutions to the problems, the second group pursuing solutions based on multi-wavelength technology. Among others patents of the first group are:

European patent application No. EP 575712 A2 to University of Manitoba of Canada which discloses a method and a device for measuring blood parameters, according to which method the changes in the directly emerging light and the scattered light of a photometric measurement are compared to one or more references to take into account the effect of change in the light scatter, e.g. from the blood sodium concentration. According to this method and device a minimum of two detecting means provide for light detection, the first detection means detecting the directly emerging light, the second detection means, and further means in case more than two detection means are provided, detecting the scattered light. Upon comparison to simultaneous measurements on references or to computed references stored in the system, the scattering distribution profile of the sample at hand is calculated, and the scattering accounted for. As will be obvious the reliability of the method and the device is dependent on the availability of proper references.

U.S. Pat. No. 5,385,539 to Advanced Haemotechnologies of the United States of America which discloses an apparatus and a method for on-line measurements of the HCT values of blood based on a minimum of two light detecting means. The first of said minimum of two light detecting means is positioned to receive light which has not been scattered or has been scattered only slightly, i.e. by a small scattering angle, the second of said minimum of two light detecting means being positioned to receive light which has been scattered by a higher angle, i.e. light which has travelled a larger distance across the blood sample. The system further includes a light intensity regulating means for regulating the light emitted to such intensity that the received light on one of the detecting means is at a constant value. In this way the received light at the other detecting means is a linear representation of the HCT value. In a preferred embodiment of the invention optical fibers are used as conveying means for transmission of light. The patent further discloses an experimental set-up in which a "back-scatter" geometry is applied, according to which the detection means is positioned on the same side of the blood sample as the light emission source.

U.S. Pat. No. 5,601,080 to Coretech Medical Technologies Corporation of Canada which discloses a method and an apparatus applying light sources and detecting means for on-line spectrometric measurements of blood parameters, the method and apparatus being characterised by included more than one light source or more than two detectors.

International patent application No. WO 96/37767 to LXR Biotechnology Inc. of USA which discloses the use of a wide angle scattering detector which applies a collector for highly scattered light which is subsequently led to a separate detector and specifically determined.

Japanese patent application No. JP 10132728 A to Nippon Koden Corporation of Japan which discloses a pattern of concentrically distributed detectors collecting the light scattered to scattering angles $\alpha$ upon measurements on white blood cells. The set-up further has leading-out sections corresponding to each of the specific circular areas of the detection pattern.

U.S. Pat. No. 5,963,335 to Waters Instruments of USA which discloses a method and an apparatus for measurements of radiation absorbance, in particular absorbance in samples of whole blood, comprising in the light path between the source and the detector an occluder. The occluded radiation pattern of three measurements, characterised by the occluder being in three different positions, are compared to factor out radiation attenuation.

The geometries and approaches disclosed in the above patents and patent applications may reduce the influence from a variable scattering coefficient, however, they are complex as they require sophisticated, expensive experimental set-ups and complicated operation or they fail to address the complete spectrum of problems as described above.

The second group of approaches, focused on multi-wavelength technology, say spectrometry, includes among others:

International patent application No. WO 94/08237 to the University of Texas System of the United States of America which discloses a method and apparatus for accurate spectrophotometric determinations of the concentrations of a number of specific hemoglobin species in whole blood samples according to which a whole blood sample is irradiated with a plurality of radiation wavelengths selected by their ability to distinguish the hemoglobin species at minimum scatter and maximum absorbance. According to the method an excess of wavelengths compared to the number of specific hemoglobin species sought is applied along with an approach, according to which the various light-scattering losses are treated as functions of the wavelengths and of the concentrations of the specific hemoglobin species. The species concentrations are calculating based on predetermined molar extinction coefficients. The patent application further discloses the use of a large detector which reduces the problem of scattering beyond the detection range.

European patent No. EP 210417 B1 to Radiometer A/S of Denmark which discloses a method and apparatus for spectroscopic determinations of (n−1) specific hemoglobin species, based on exposing a turbid sample of whole blood or hemolysed blood with light of at least n different wavelengths and measuring along with the (n−1) hemoglobin species at least one turbidity component, subsequently calculating the species concentration from predetermined molar extinction coefficients.

European patent application No. EP 800074 A1 to AVL Medical Instruments AG of Switzerland which discloses the use of two detection geometries and the use of n different wavelengths and 2n measuring values for the determination of n hemoglobin species, calculating the species concentration from predetermined molar extinction coefficients. The detector geometries may include optical means like a lens for improved separation between directly transmitted and scattered light.

The methods and devices of spectrometric technology display a thorough approach to the elimination of the problems as related to variable scattering coefficients, in that such technology addresses directly the scattering phenomena. The spectrometric multi-wavelength approaches, however, are complex as they require sophisticated and expensive experimental set-ups and demand complicated operation.

Therefore, there is still a need for a simple method and a simple apparatus for accurate optical measurements on samples of variable scattering coefficient, in particular on blood samples of variable scattering coefficient. Especially, there is a need for a simple method and a simple apparatus which provide correction for the influence of variations in the effective optical pathlength, detector sensitivity as well as in undetected light as caused be reflection and scattering beyond the detector.

This has been achieved by the apparatus for optical measurements on light scattering samples according to the invention comprising at least one light emission means, a sample cuvette with a sample chamber, a filter and a detecting means, the apparatus being characterised in that the filter is positioned in the light path between the sample cuvette and the detecting means and that the filter is an absorption filter having an absorbance which decreases progressively from the center towards the periphery of the filter.

According to a preferred embodiment of the invention the apparatus for optical measurements is an apparatus for optical measurements of the concentration of any of hemoglobin, oxyhemoglobin, deoxyhemoglobin, methemoglobin, carboxyhemoglobin, sulfhemoglobin, bilirubin, diagnostic dyes and/or any other light absorbing compound, preferably of the concentration of hemoglobin, and/or of the level of oxygen saturation, of a sample of whole blood.

An absorption filter is defined as a filter, which provides absorption of light due to a light absorbing chemical compound like a metal or a metal oxide which is deposited onto or incorporated into a carrier like a glass or polymer foil. Thus the absorption filter may be a multilayered structure or a single layered structure.

The absorption filter absorbs light of a range of wavelengths, which may be narrow in that e.g. only green light is absorbed, or which may be broad in that e.g. any visible light is absorbed, the absorptivity being independent on the angle of incidence of the light reaching the filter surface. The light absorbing chemical compounds of the absorption filter may be selected so as to absorb ultraviolet, visible or infrared light as appropriate.

The light absorbing chemical compound of the absorption filter may be deposited or incorporated as a macroscopic pattern of completely absorbing raster. At a high density of raster and thus low area of bare carrier the absorption filter will display high absorbance. Similar, at a low density of raster and thus high area of bare carrier the absorption filter will display low absorbance. Although the absorbance based on raster is non-uniform on a microscopic scale, it is uniform on a macroscopic scale.

The light absorbing chemical compound may as well be deposited or incorporated on a microscopic scale to provide a homogenous colouring or a shading, i.e. a partial absorption, e.g. as obtained by a sputtering technique. Thus dark shadings provide high absorbance whereas light shadings provide low absorbance. Absorbance based on shading is uniform on the microscopic scale as well as on the macroscopic scale.

The absorbance $F(\alpha'_n)$ in an annular zone of the absorption filter characterised by a range of scattering angles $\alpha'_n$ between the scattering angels $\alpha_{n-1}$ and $a_n$, is defined as the logarithm of the ratio of the intensity of light of a given wavelength incident onto and the intensity of light of said given wavelength transmitted across the annular zone.

Thus, the absorption filter of the present invention is characterised in that for any two annular zones of the filter, characterised by the range of scattering angles $\alpha'_s$ and $\alpha'_t$, the corresponding absorbances being $F(\alpha'_s)$ and $F(\alpha'_t)$, $F(\alpha'_s) > F(\alpha'_t)$ in case $\alpha'_s < \alpha'_t$, say in case the scattering angle range $\alpha'_t$ is more peripheric than the scattering angle range $\alpha'_s$.

The absorbance $F(\alpha'_n)$ may be provided by any distribution of absorbing zones within the annular zone characterised by the range of scattering angles $\alpha'_n$. Accordingly, the complete annular zone may display uniform absorbance or it may display subzones of uniform maximum absorption and no absorbance in the remaining subzones.

Alternatively, the apparatus for optical measurements on light scattering samples according to the invention comprises a light emission means, a sample cuvette with a sample chamber, a filter and a detecting means, the apparatus being characterised in that the filter is positioned in the light path between the sample cuvette and the detecting means, and that the filter is an interference filter selected from the groups of band pass filters and long wavelength pass filters of a center and a cut-off wavelength, respectively, which are longer than the wavelength of the light from the light emission means, preferably longer by between 1 and 25%, more preferably between 5 and 20%, even more preferably between 10 and 20%.

The Interference filters may have center or cut-off wavelengths corresponding to ultraviolet, visible or infrared light as appropriate.

The filter may be provided as a separate component or as an integrated part of the sample cuvette, e.g. printed directly onto the light exit window of the sample cuvette, or an integrated part of the detector. Accordingly, the sample cuvette with an integrated filter may be a disposable unit for use in one or a few measurements only.

Thus, the invention further covers a sample cuvette for optical measurements on light scattering samples comprising a sample chamber and an absorption filter, the sample cuvette having light entry and light exit windows, respectively, on the walls defining the sample chamber, and further being characterised in that the absorption filter is an integrated part of the sample cuvette positioned on or into the exit window of the sample cuvette and that the absorption filter has an absorbance which decreases from the center towards the periphery of the filter.

Still further, the Invention covers a sample cuvette for optical measurements on light scattering samples comprising a sample chamber and an interference filter, the sample cuvette having light entry and light exit windows, respectively, on the walls defining the sample chamber, and further being characterised in that the interference filter is an integrated part of the sample cuvette positioned on or into the exit window of the sample cuvette and that the interference filter is selected from the groups of band pass filters and long wavelength pass filters.

The sample cuvette may be made entirely from light transmittive materials or the cuvette walls may have defined light transmittive areas providing entry and exit windows for the light. In the former case the windows are not seen as delimited areas. The term window is used herein to cover both embodiments as a designation of the area of the sample chamber and cuvette walls where light enters and exits.

The detecting means of the apparatus of the present invention may be a detector of such large area that it covers a broad range of scattering angles. Thus, it is preferred that the detector covers scattering angles a up to 70°. The distance between the center of the sample chamber and the detector may be up to 1.5 mm, and accordingly the detector preferably has an active area which is not less than approx. 25 mm².

In order to reduce the reflection of light an optical coupling may be introduced in the apparatus between the sample chamber and the filter and/or between the filter and the detector. Such optical couplings may be layers of glycerols, silicones or acrylates, and may have a thickness in the range 1–100µ.

The apparatus may further include an aperture which is placed between the light source and the sample cuvette. The aperture may have a circular symmetry or it may have a symmetry different from the circular symmetry. In both cases the filter may have a symmetry corresponding thereto. Accordingly, as the scattering phenomenon in itself has a circular symmetry, the filter symmetry corresponding to e.g. a rectangular aperture is ellipsoid.

The invention further covers a method, according to which the apparatus or the sample cuvette of the present invention are used for optical measurements on light scattering samples, in particular for optical measurements of blood parameters, especially the total hemoglobin concentration. The apparatus and method of the present invention, however, is not restricted to optical measurements of the total hemoglobin concentration, but cover also optical measurements of specific hemoglobin derivatives like oxyhemoglobin, deoxyhemoglobin, methemoglobin, carboxyhemoglobin and sulfhemoglobin along with bilirubin, diagnostic dyes and/or any other light absorbing compound present in the blood. The oxygen saturation of whole blood may be determined by the optical method as well.

Measurements may be conducted under flow conditions as well as under non-flow conditions. Further, the optical measurements may be conducted using one wavelength, preferably an isobestic wavelength, however, they may as well be conducted using a plurality of wavelengths for the simultaneous determination of a plurality of concentrations and/or parameters, with the proviso that in the case of the filter being an interference filter only one wavelength is used.

According to a preferred embodiment of the method of the invention optical measurements are conducted using at least 2 wavelengths, preferably 2 wavelengths, for the simultaneous determination of the hemoglobin concentration and the oxygen saturation level of blood samples.

The method and apparatus for optical measurements under conditions of variable scattering coefficients are described based on the applicants experience from measurements on whole blood. The invention, however, is not restricted hereto. As will be obvious from the description of the invention, the principles of the method and apparatus are applicable for optical measurement on any sample of variable scattering coefficient, whether biological, physiological or chemical. Among others, such samples include samples of milk, waste water and paints.

The absorption filter of the present invention has an absorbance which decreases progressively from the center towards the periphery of the filter. Such a filter is capable of correcting for those variations of the scattering coefficient which relate to variations in the detector sensitivity and the effective optical pathlength.

The detector sensitivity varies continuously with the angle of incidence of the light. Accordingly it has been found, that most optical detectors have an angular dependent sensitivity which can be modelled as an angular range dependent vector of detector angular absorbances (DAA) counted in the dimensionless units of absorbance.

Thus the vector of DAA's refers to the absorbance as observed over separate ranges of scattering angles $\alpha'_1$, $\alpha'_2$, $\alpha'_3$, ..., $\alpha'_n$, ..., $\alpha'_{max}$, where $\alpha'_1$ refers to the central range of small scattering angles between $\alpha_0=0°$ and $\alpha_1$, $\alpha'_n$ refers to any range of scattering angles between $\alpha_{n-1}$ and $\alpha_n$, and $\alpha'_{max}$ refers to the range of the largest scattering angles detectable by the detector means, in this case between the angles $\alpha_{max-1}$ and $\alpha_{max}$, the maximum detectable angle. In such case the vector of DAA's is characterised by (DAA($\alpha'_1$), DAA($\alpha'_2$), DAA($\alpha'_3$), ..., DAA($\alpha'_n$) ..., DAA($\alpha'_{max}$)).

Any mathematical function DAA($\alpha$) which corresponds to the detector angular absorbances may as well be used for the modelling. One group of such functions is trigonometric functions, in particular cosine functions, although other functions may be used for the modelling as well.

At a given sample absorption, the effective optical pathlength varies continuously with the scattering angle. Accordingly it has been found that scattering contributes to absorbance in a way which can be modelled as an angular range dependent vector of pathlength angular absorbances (PAA) counted in the dimensionless units of absorbance.

Whereas the vector of DAA's is independent on the sample absorption, the vector of PAA's depends thereon.

Thus the vector of PAA's refers to the absorbance as observed over separate ranges of scattering angels $\alpha'_1$, $\alpha'_2$, $\alpha'_3$, ..., $\alpha'_n$, ..., $\alpha'_{max}$, defined as above, where the vector of PAA's is characterised by (PAA($\alpha'_1$), PAA($\alpha'_2$), PAA($\alpha'_3$), ..., PAA($\alpha'_n$) ..., PAA($\alpha'_{max}$)) for a given sample absorption.

Any mathematical function PAA($\alpha$) which corresponds to the pathlength angular absorbance may as well be used for the modelling. In a simple approach it may be assumed that scatter to the scattering angle $\alpha$ takes place at the center of the sample, and that no multiple, say no further scattering, occurs. Compared to the optical pathlength d of unscattered light, scattered light will now travel the distance d($\alpha$)=0.5d+0.5d/cos $\alpha$. Based on such mathematical modelling, and on the boundary conditions, functions PAA($\alpha$) may now be determined.

Thus, in order to correct for variations in the detector sensitivity and the effective optical pathlength, the absorption filter has an angular range dependent absorbance F as observed over separate ranges of scattering angles $\alpha'_1$, $\alpha'_2$, $\alpha'_3$, ..., $\alpha'_n$, ..., $\alpha'_{max}$, characterised by the absorbance F($\alpha'_n$)=ABS$_{max}$−(DAA($\alpha'_n$)+PAA($\alpha'_n$)), which decreases from the center towards the periphery of the filter, where ABS$_{max}$ is the maximum absorbance of the filter which is applied in the central angular range $\alpha'_1$.

The maximum filter absorbance ABS$_{max}$ is equal to or larger than DAA($\alpha'_{max}$)+PAA($\alpha'_{max}$), say the absorbances as ascribed to the detector angular sensitivity and effective optical pathlength in the outer angular range $\alpha'_{max}$. Preferably ABS$_{max}$ is equal to DAA($\alpha'_{max}$)+PAA($\alpha'_{max}$).

Absorption filters may also be referred to as transmittive filters or transmittance filters. In the prior art, such filters of progressively decreasing absorbance are known in the field of optics:

U.S. Pat. No. 4,298,275 to Xerox Corporation of USA discloses a wide angle exposure system for a copier including a filter, which has an absorption profile characterised by an absorbance decreasing progressively from the center towards the periphery of the filter. Similar, U.S. Pat. No. 4,906,081 to Ricoh Company, Ltd. of Japan discloses a filter displaying a symmetrical absorbance profile ranging from minimum absorbance at the axial center, via maximum absorbance in an annular zone around the axial center to minimum absorbance at the periphery of the filter, the filter being used for image forming optical systems.

Neither '275 nor '081, however, disclose any teaching of absorption filters of decreasing absorbance being used in the light path of an apparatus for optical measurements on light scattering samples. In particular, the patents do not teach anything on the use of such filters to reduce the problems related to optical measurements dominated by variable scattering coefficients. Therefore, to the best of the knowledge of the applicants, the apparatus, sample cuvette and method of the present invention are novel.

In one embodiment of the invention the number of annular zones n of the absorption filter is between 2 and 10, preferably between 2 and 7. More preferably n is 5.

Accordingly, at a hemoglobin concentration of approx. 15 g/dl which is the normal concentration in human blood, the below absorption filter of five scattering angle ranges has been found to provide excellent correction for variations due to scattering.

Thus, this absorption filter displays an absorbance $F(\alpha'_n)$, as described from $\alpha'$-ranges of 0°–20°, 20°–40°, 40°–50°, 50°–60° and 60°–, respectively, of $F(0°-20°)=ABS_{max}=0.40-0.90$, $F(20°-40°)=0.25-0.60$, $F(40°-50°)=0.10-0.40$, $F(50°-60°)=0.05-0.25$ and $F(60°-)=0.00$, and where further, at any two scattering angle ranges $\alpha'_s$ and $\alpha'_t$, $F(\alpha'_s)>F(\alpha'_t)$ in case $\alpha'_s<\alpha'_t$, say if the scattering angle range $\alpha'_t$ is more peripheric than the scattering angle range $\alpha'_s$.

In a further preferred embodiment of the invention the absorbance $F(\alpha'_n)$ is $F(0°-20°)=ABS_{max}=0.50-0.80$, $F(20°-40°)=0.30-0.50$, $F(40°-50°)=0.15-0.30$, $F(50°-60°)=0.05-0.15$ and $F(60°-)=0.00$, and where further, at any two scattering angle ranges $\alpha'_s$ and $\alpha'_t$, $F(\alpha'_s)>F(\alpha'_t)$ in case $\alpha'_t$ is more peripheric than $\alpha'_s$.

For those samples of blood with a hemoglobin concentrations higher or lower than 15 g/dl the above filter provides correction as well, however, only partial as compared to the optimal correction in the 15 g/dl case.

In an alternative embodiment of the invention, the filter displays an absorbance, which is modelled by any mathematical function $G(\alpha)=ABS_{max}-(DAA(\alpha)+PAA(\alpha))$, where all of $ABS_{max}$, $DAA(\alpha)$ and $PAA(\alpha)$ are defined above.

In a preferred embodiment of the invention the absorption filter consists of a polyester foil of a thickness of 20–150 $\mu$m onto which a silver raster pattern of a thickness of 0.1–5 $\mu$m and a raster size of 10–200 $\mu$m has been photographically developed.

In an alternative embodiment of the invention, the apparatus comprises an interference filter, which is of the band pass filter type or of the long wavelength pass filter type of a center and a cut-off wavelength, respectively, which are longer than the wavelength of the light from the light emission means, preferably longer by between 1 and 25%, more preferably between 5 and 20%, even more preferably between 10 and 20%, and which is positioned in the apparatus between the sample cuvette and the detecting means.

The interference filters of the present invention display uniform transmission across the full filter area, and do not require precise centering as compared to the absorption filters. They consist of a carrier like a glass or polymer foil, onto which optical interference layers of metals have been deposited.

Interference filters of the said groups shift their center wavelength and cut-off wavelength, respectively, to shorter wavelengths upon exposure to light of lower angles of incidence compared to light of angle of incidence $\beta=90°$. Accordingly, light of the wavelength of the measurement is fully transmitted only if it has a low angle of incidence, say a high scattering angle, whereas light of higher angles of incidence, say of low scattering angles, is only partly transmitted or not transmitted at all.

The above apparatus of the present invention comprising said interference filter provides the technical solution to the above problems of varying scattering coefficient, as it allows correction for the influence of variations in the effective optical pathlength and the detector sensitivity. In particular, when applied in the apparatus the interference filter has a resulting transmission pattern similar to the transmission pattern of the above absorption filter.

In the prior art interference filters and their use in the detecting system of apparatus for optical measurements are known. Thus, U.S. Pat. No. 4,303,336 to Baxter Travenol Laboratories of United States of America, U.S. Pat. No. 5,088,493 to Sclavo, S.p.A. of Italy, and U.S. Pat. No. 5,478,750 to Abaxis, Inc. Of Canada all describe the use of interference filters in detecting systems.

All the above patents, however, describe the use of interference filters for wavelength filtering, branching or the like, and none of the above patents disclose any teaching on an apparatus for optical measurements on light scattering samples, which is characterised in that the filters have of a center or a cut-off wavelength, respectively, which are longer than the wavelength of the light from the light emission means and that such filters display reduced transmission of light of high angle of incidence.

In one embodiment, the interference filter consists of a glass of a thickness of 100–500 $\mu$m onto which optical interference layers of metals have been deposited.

In a preferred embodiment the interference filter is a band pass filter of a center wavelength which is longer than the wavelength of the light from the light emission means, preferably longer by between 1 and 25%, more preferably between 5 and 20%, even more preferably between 10 and 20%. At a preferred experimental wavelength in the range 500–510 nm, the band pass filter preferably has a center wavelength in the range 505–630 nm, more preferably in the range 530–600 nm, even more preferably in the range 550–600 nm.

In another preferred embodiment the interference filter is a long wavelength pass filter of a cut-off wavelength which is longer than the wavelength of the light from the light emission means, preferably longer by between 1 and 25%, more preferably between 5 and 20%, even more preferably between 10 and 20%, and which has a steepness of 0.5–2% (absorption) per nm. At a preferred experimental wavelength in the range 500–510 nm, the long wavelength pass filter has a cut-off wavelength in the range 505–630 nm, more preferably in the range 530–600 nm, even more preferably in the range 550–600 nm.

Whereas the use of the filter in the apparatus is focused on correcting for variations of the detector angular sensitivity and effective optical pathlength, undetected light is mainly accounted for by the use of a large area detector covering a broad range of scattering angles.

Thus, in a preferred embodiment of the invention the detector has a detection range, defined by the scattering angle α, of at least 0–50°, preferably 0–65°, more preferably 0–70°. The detector may be any detector applicable for detection of light of the wavelength applied, preferably, however, the detector is a silicon photo diode.

In another preferred embodiment of the invention the distance between the center of the sample chamber and the detector is in the range 0.2–1.5 millimeter, preferably 0.2–1.0 millimeter, more preferably 0.5–1.0 millimeter. Accordingly, the detector has an active area, which is not less than 25 mm². Preferably the detector area is not less than 70 mm², more preferably not less than 100 mm².

In order to reduce reflection of light in the light path optical couplings may be introduced in the apparatus. Thus, in one preferred embodiment of the invention the apparatus further comprises at least one optical coupling which is positioned between the sample and the filter and/or between the filter and the detecting means. Such optical couplings are thin layers of low absorbance materials, preferably of refractive index similar to the refractive index of their neighbouring components. The material of such optical couplings should be chemically stable, in particular towards oxidation.

Thus, optical coupling layers are made from glycerols, silicones or acrylates, preferably from silicon oils, silicone resins or acrylate resins which are applied in layers of a thickness in the range 1–100 µm, preferably 5–50 µm.

In a preferred embodiment the apparatus includes an aperture which is placed between the light source and the sample chamber. Preferably the aperture has an area not larger than 1 mm².

For the optimisation of the absorption filter according to the present invention a procedure is applied which is based on empirical information on the detector angular sensitivity and on the absorbance and scattering on selected blood samples.

Accordingly, the vector of DAA's is estimated based on detector specifications as well as from blank experiments, exposing the detector to light of varying angle of incidence. The vector of PAA's is estimated from empirical data on scattering and absorbance of samples of whole blood, preferably on samples of whole blood of a typical hemoglobin concentration of approx. 15 g/dl and varying scattering coefficient. Based on these vector estimates, a series of filters are constructed with varying values of $ABS_{max}$ and $α_{max}$. Based on a mapping of the errors in terms of experimentally found hemoglobin concentration, e.g. vs. the MCHC value, as obtained upon variation of those two parameters, the optimal filter is designed.

For the optimisation of the interference filter according to the present invention a series of filters are constructed with varying band width and center wavelength for band pass filters and stepness and cut-off wavelengths for long wavelength pass filters, respectively. Based on a mapping of the errors in terms of experimentally found hemoglobin concentration, e.g. vs. the MCHC value, as obtained upon variation of those two parameters, the optimal filter is designed.

Measurements may be conducted under flow conditions, i.e. the sample flowing through the sample chamber during measurement, as well as under non-flow conditions. In particular, the simple method and apparatus of the invention allow fast measurements, which reduce aggregation and precipitation in samples of whole blood. As further the method addresses particularly the problem of scattering due to blood cell aggregation the method is especially adapted to non-flow measurements.

The optical measurements may be conducted using one wavelength, however, they may as well be conducted using a plurality of wavelength for the simultaneous determination of a plurality of concentrations and/or parameters. In the case the filter is an interference filter, only one wavelength is used.

Preferably measurements are done at an isobestic wavelength, i.e. in the case of tHb at a wavelength at which the extinction coefficients of oxyhemoglobin and deoxyhemoglobin are the same. One such preferred wavelength is 506.5 nm.

FIG. 1 displays an exploded view of the apparatus of the present invention.

FIG. 2 illustrates the principle of absorption filters and interference filters, as well as their use in the apparatus of the present invention.

FIG. 3 displays the absorption filter with annular zones of uniform absorbance of FIG. 1.

FIG. 4 displays the absorbance vs. radius for the absorption filter of FIG. 1.

FIG. 5 displays the mathematical modelling of the absorbance of the absorption filter of FIG. 1.

FIG. 6 displays an absorption filter with annular zones displaying subzones of uniform maximum absorbance and no absorbance in the remaining subzones.

Figure 1:
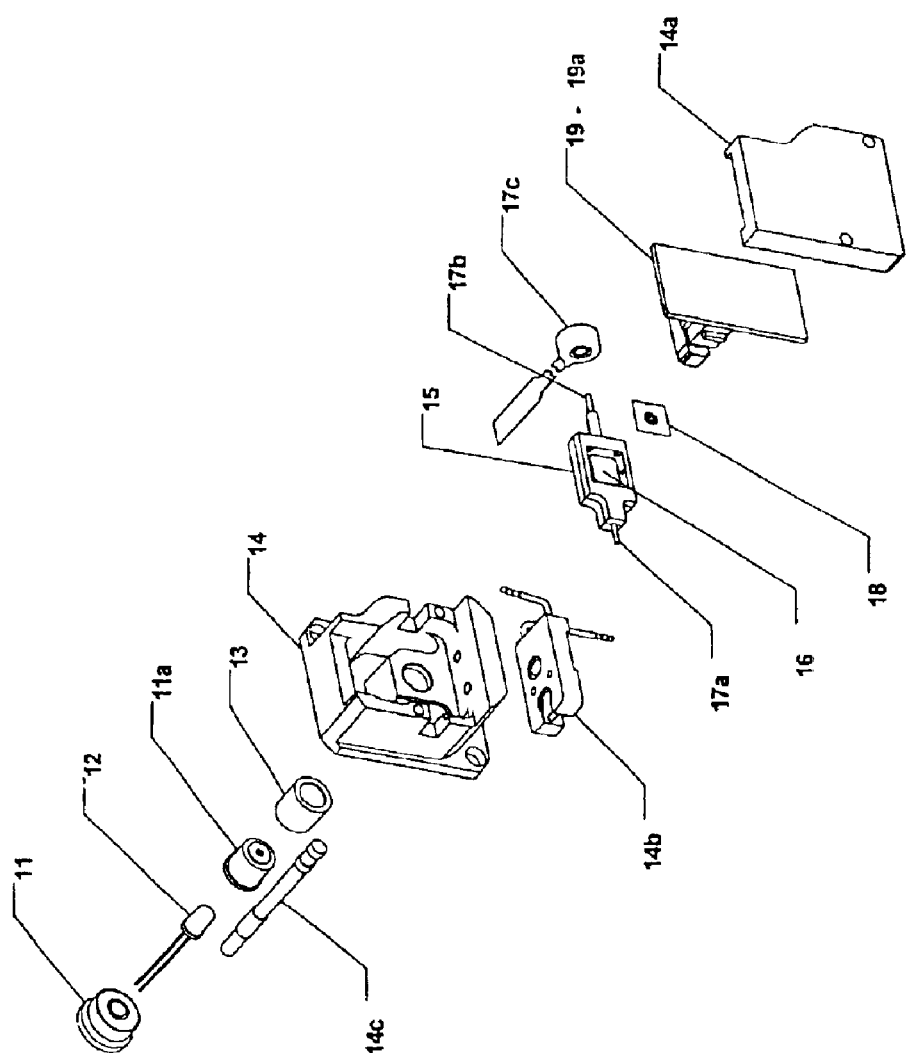

With reference to FIG. 1, which is an exploded view of the apparatus of the present invention, the apparatus includes a light emission means 12 which is a diode HLMP-CE23-R0000 from Hewlett Packard, positioned by two polymer guides 11 and 11a, the latter including an aperture of an area of 1 square millimeter.

A band pass filter of a center wavelength of 506.5 nm from Ferroperm Optic, Denmark, 13, defines the wavelength of the light which enters the cuvette house 14 and 14a. The sample cuvette 15 carries a second aperture of an area of 1 square millimeter (not shown). The sample cuvette 15 further has a light transmittive entry window (not shown) and a light transmittive exit window 16, defining a sample chamber of a thickness of 0.1 mm (not shown). In addition, the sample cuvette 15 is connected to the sample inlet 17a and outlet 17b and to a liquid sensor 17c.

The thermostat jacket 14b heats the cuvette house 14 and 14a to 37° C., monitored by the thermocouple 14c.

The absorption filter 18 consists of a polyester foil of a thickness of 100 µm onto which a silver raster pattern of a thickness of 1 µm and a raster size of 84 µm has been photographically developed. The filter has an absorbance of F(0°–20°)=0.60, F(20°–40°)=0.40, F(40°–50°)=0.22, F(50°–60°)=0.10 and F(60°–)=0.00. The filter is positioned in the light path on the surface of the detector 19 which is a 25 mm² silicon photo diode OPR 5913 from Optek, USA and which is not shown in the view.

The detector 19 is connected to the detector electronic circuit 19a and is positioned in a distance 1.05 mm from the center of the sample chamber.

Not shown in FIG. 1 are optical couplings of thin layers of glycerol which are positioned between the sample cuvette and the filter and between the filter and detector.

Figure 2:
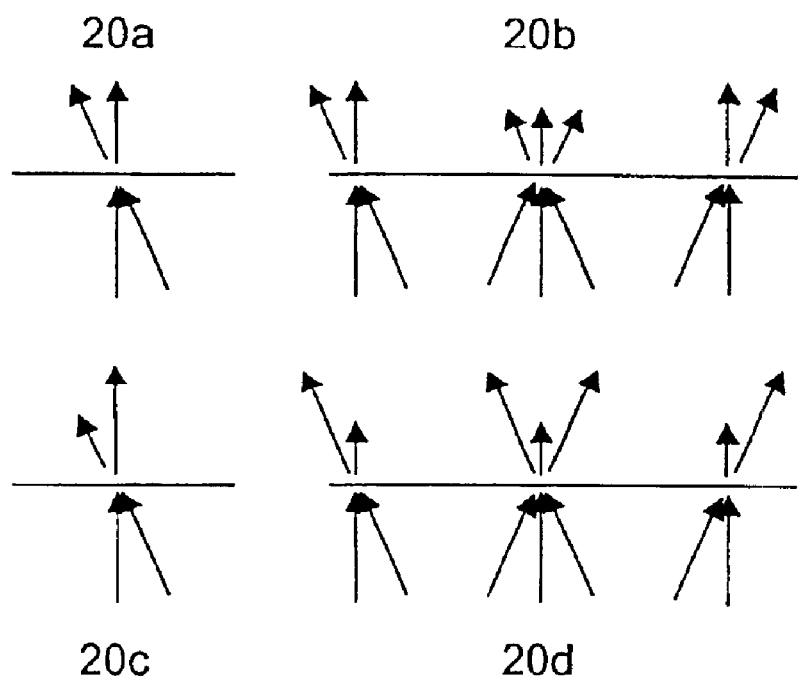

Referring to FIG. 2, the schematic 20a shows the principle of an absorption filter with a deposited raster pattern of a light absorbing chemical, the length and the slope of the arrows indicating the intensity and the angle of the light reaching and leaving the filter, respectively. The absorbance of the absorption filter is characterised in that it is independent on the angle of incidence of the light reaching the filter surface, i.e. similar reductions of the light intensity is observed for light of angle of incidence $\beta=90°$ and for light of lower angle of incidence. When applied in the apparatus of the present invention, as shown in schematic 20b, the absorption is still independent on the angle of incidence. The apparatus and the absorption filter of the present invention, however, has an absorbance which is maximum at the center of the filter and decreases towards the periphery and thus the intensity reduction is higher at the center compared to at the periphery.

In the case of an absorption filter with a homogenous colouring or a shading, the filter has a self-absorbance, which depends on the effective optical pathlength within the filter shading and thus on the angle of incidence. Accordingly, the intensity of light of low angle of incidence is further reduced compared to schematic 20a and 20b.

The schematic 20c shows the principle of an interference filter. In 20c, a band pass filter is irradiated with light corresponding to the filter center wavelength. In such case light of angle of incidence $\beta=90°$ is fully transmitted. Due to the shift of the filter center wavelength as described above, however, light of a lower angle of incidence is only partly transmitted. It should be understood, that the transmission of interference filter is uniform over the full filter area.

Turning to the application of the filter in the apparatus of the present invention 20d, a band pass filter of a center wavelength which is longer than the experimental wavelength is applied. Due to shift of the center wavelength, however, light of angle of incidence $\beta=90°$ is now only partly transmitted, whereas light of a lower angle of incidence is fully transmitted. According to the invention light reaching the surface of the filter at the center in fact has an angle of incidence $\beta$ equal to or close to 90°, whereas light reaching the filter at the periphery has a lower angle of incidence. Thus light is transmitted in accordance with the schematic 20d, i.e. partly at the filter center and fully at the filter periphery.

Figure 3:
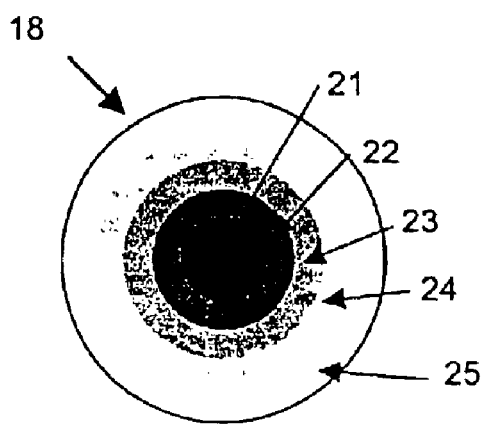

FIG. 3 shows the absorption filter 18 of FIG. 1, the absorbance of which decreases progressively from the center towards the periphery. As described above, the filter displays five annular zones of uniform absorption 21–25, the absorbance decreasing progressively from the center annular zone 21 towards the peripheric annular zone 25.

Figure 4:
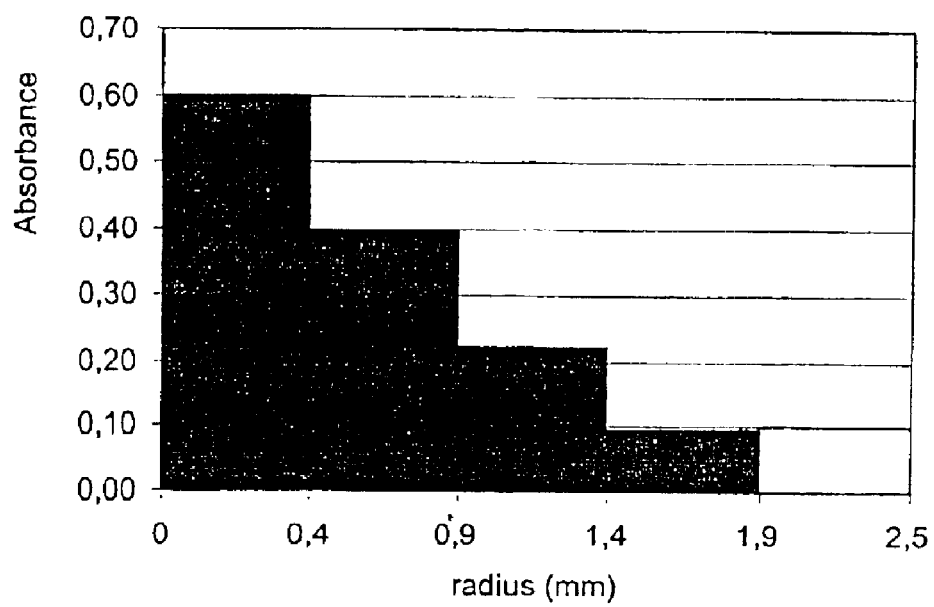

FIG. 4 shows the absorbance vs. radius for the absorption filter of FIGS. 1 and 3. Accordingly, the absorbance is 0.60 in the radius range 0–0.4 mm, 0.40 in the range 0.4–0.9 mm, 0.22 in the range 0.9–1.4 mm, 0.10 in the range 1.4–1.9 mm, respectively. For radii larger than 1.9 mm, the filter shows no absorbance.

Figure 5:
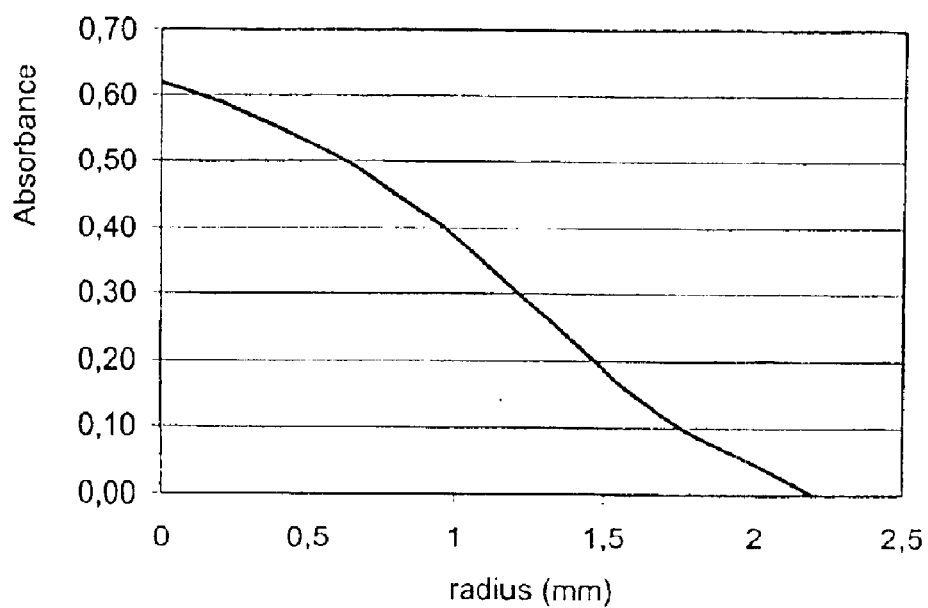

FIG. 5 displays the mathematical modelling of the absorption filter of FIGS. 1 and 3–4. Such modelling provides the exact mirroring of the correction for the absorbances as ascribed to the variation in detector sensitivity and effective optical pathlength. For simplicity, the mathematical modelling of the absorption filter may be approximated with the annular zone absorption filter of FIGS. 1 and 3–4.

Figure 6:
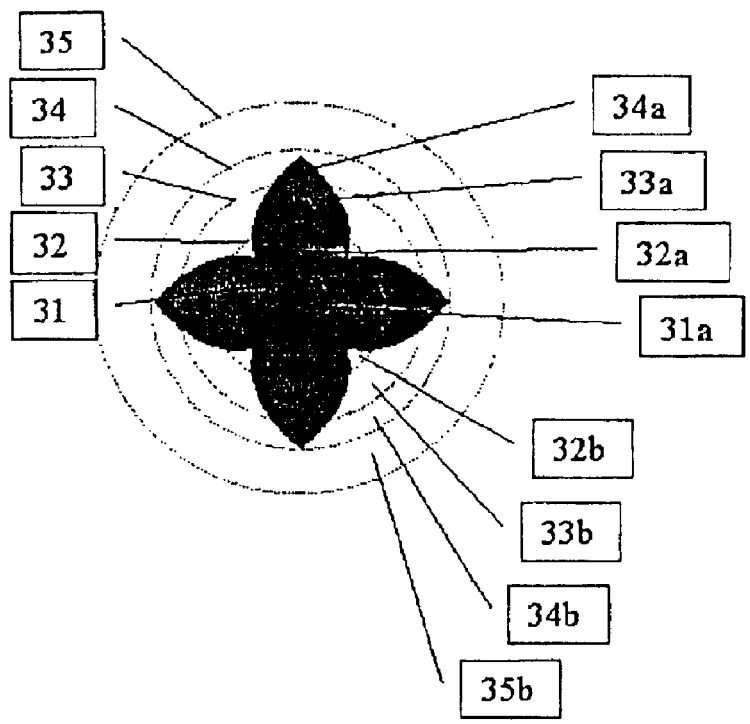

FIG. 6 displays an absorption filter of an absorbance which decreases progressively from the center towards the periphery, and in which the individual annular zones display subzones of uniform, maximum absorbance $ABS_{max}$ and subzones of no absorbance. The absorption filter pictured displays five annular zones 31–35. Thus, the full subzone 31a of the center annular zone 31 displays uniform, maximum absorbance. 32–34 are annular zones with subzones of uniform, maximum absorbance 32a–34a and subzones of no absorbance 32b–34b. The full subzone 35b of the peripheric annular zone 35 displays no absorbance. Accordingly, the absorbance decreases progressively from the center towards the periphery as the subzones of maximum absorbance are decreased relative to the subzones of no absorbance.

Figure 7:
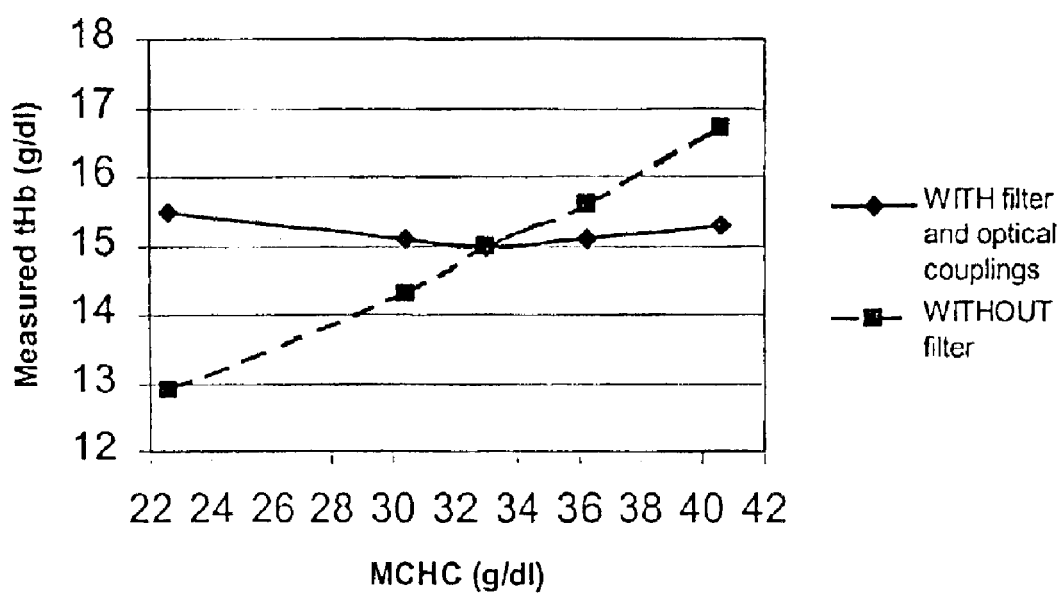
FIG. 7 illustrates the experimentally found total hemoglobin concentrations as obtained with and without the filter of the present invention.

FIG. 7 illustrates the experimentally found total hemoglobin concentrations as obtained with and without the filter of the present invention, using the apparatus and the absorption filter of FIGS. 1 and 3–4, cf. Example 1 and Comparative Example 1.

Figure 8:
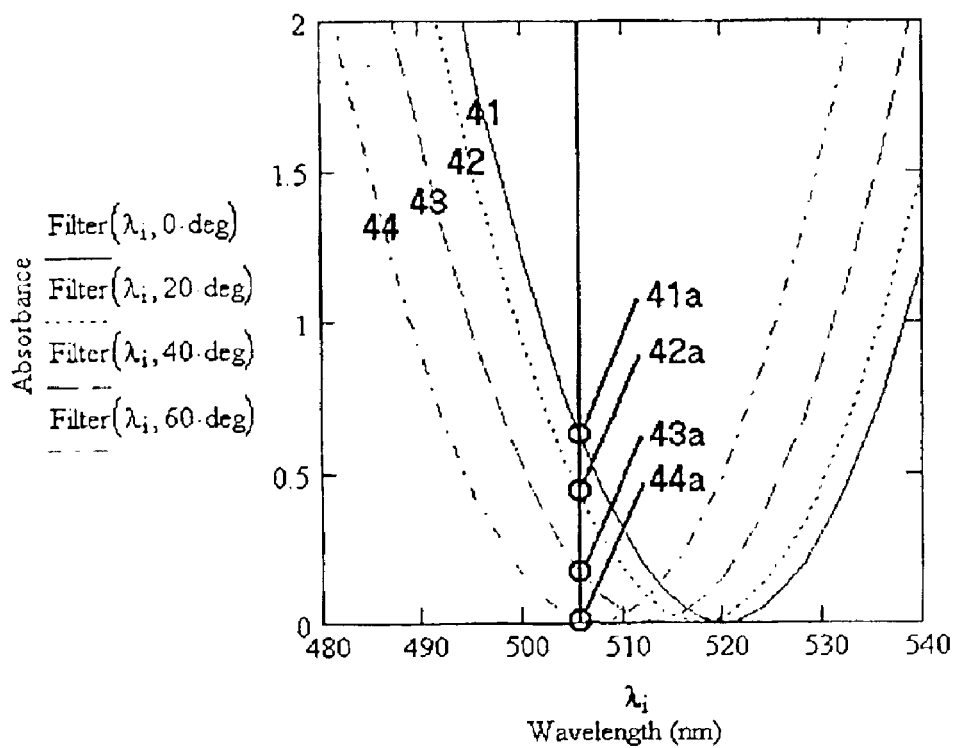
FIG. 8 illustrates the principle of the use of interference filters in the apparatus of the present invention.

FIG. 8 illustrates the principle of using interference filters in the apparatus of the present invention. The figure shows the absorbance characteristics of a band pass filter of a center wavelength of 520 nm. The center wavelength is shifted to shorter wavelengths upon exposure to light of higher scattering angles (42:20°, 43:40° and 44:60°) compared to unscattered light (41:0°). According to the invention, as light of a wavelength 13.5 nm shorter than the center wavelength of the filter is applied for the measurement, i.e. 506.5 nm, absorbance decreases with increasing angle of scattering, as observed at 41a: absorbance 0.6 at 0°, 42a: absorbance 0.4 at 20°, 43a: absorbance 0.1 at 40° and 44a: absorbance 0.0 at 60°.

Figure 9:
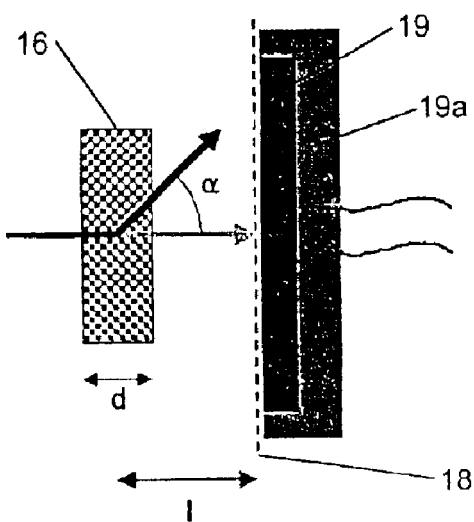
FIG. 9 shows the geometry of scattering, the filter and the detector.

FIG. 9 shows the scattering, filter and detector geometry. The scattering of light to a scattering angle $\alpha$ is assumed to take place in the center of the sample chamber 16 of a thickness d=0.1 mm, the filter 18 and the detector 19 with a detection range defined by the scattering angle $\alpha$ of 0–70°, being positioned in a distance l=1.05 mm from the center of the sample chamber.

EXAMPLE 1

Optical measurements were conducted on samples of whole blood, using an apparatus according to FIG. 1.

The experiment was conducted at 37° C. on five samples, each of a tHb value of 15.0 g/dl, however, with MCHC values of 22.6, 30.4, 33.0, 36.3 and 40.6 g/dl, respectively.

The apparatus was calibrated using a sample of tHb 15.0 g/dl and MCHC 33 g/dl. Thus, at MCHC 33 g/dl which is the normal MCHC value, the experimentally found tHb value was 15.0 g/dl.

At MCHC 30.4 g/dl, as well as at MCHC 36.3 g/dl, tHb values of 15.1 g/dl were found. At MCHC 22,6 g/dl a tHb of 15.5 g/dl was found, whereas the experimental value of tHb was 15.3 g/dl at MCHC 40.6 g/dl.

COMPARATIVE EXAMPLE 1

In an experiment similar to example 1, however, with no filter and optical couplings in the light path, the tHb's were determined as well.

The apparatus excluding filter was calibrated using a sample of tHb 15.0 g/dl and MCHC 33 g/dl. Thus, at MCHC 33 g/dl, the experimentally found tHb value was 15.0 g/dl.

At MCHC 30.4 g/dl, a tHb value of 14.3 g/dl was found, whereas at MCHC 36.3 g/dl, a tHb of 15.6 g/dl was found. At MCHC 22.6 g/dl a tHb of 12.9 g/dl was found, whereas the experimental value of tHb was 16.7 g/dl at MCHC 40.6 g/dl.

What is claimed is:

1. An apparatus for optical measurements on light scattering samples comprising at least one light emission means (12), a sample cuvette (15) with a sample chamber and a detecting means (19), the apparatus being characterised in that it comprises
an absorption filter (18) which is positioned in the light path between the sample cuvette (15) and the detecting means (19), said absorption filter (18) has a center and a periphery and an absorbance which decreases from the center towards the periphery.

2. An apparatus according to claim 1 for optical measurements of the concentration of any of hemoglobin, oxyhemoglobin, deoxyhemoglobin, methemoglobin, carboxyhemoglobin, sulfhemoglobin, bilirubin and/or diagnostic dyes.

3. An apparatus according to any of the claims 1, in which the absorption filter (18) has annular zones (21–25) defined by a range of scattering angles $\alpha'_n$, each zone having an absorbance $F(\alpha'_n)$, so that for any two annular zones of the absorption filter (18), defined by the ranges of scattering angles $\alpha'_s$ and $\alpha'_t$, the corresponding absorbances being $F(\alpha'_s)$ and $F(\alpha'_t)$, $F(\alpha'_s) > F(\alpha'_t)$ in case $\alpha'_t$ is more peripheric than $\alpha'_s$.

4. An apparatus according to 3, in which the detector (19) has a detector angular sensitivity defining a detector angular absorbance $DAA(\alpha'_n)$ in the scattering angle range $\alpha'_n$ and in which the sample has an effective optical pathlength defining a pathlength angular absorbance $PAA(\alpha'_n)$ in the scattering angle range $\alpha'_n$ and in which the absorption filter (18) has an absorbance $F(\alpha'_n) = ABS_{max} - (DAA(\alpha'_n) + PAA(\alpha'_n))$, where $ABS_{max}$ is the maximum absorbance of the absorption filter.

5. An apparatus according to claim 4, in which the maximum filter absorbance $ABS_{max}$ is equal to $DAA(\alpha'_{max}) + PAA(\alpha'_{max})$, where $DAA(\alpha'_{max})$ is the detector angular absorbance in the outer angular range ($\alpha'_{max}$) and where $PAA(\alpha'_{max})$ is the pathlength angular absorbance in the outer angular range ($\alpha'_{max}$).

6. An apparatus according to any of the preceding claim 3, in which the absorption filter (18) has an absorbance in the scattering angle ranges 0°–20°, 20°–40°, 40°–50°, 50°–60° and >60°, respectively, of F(0°–20°)=0.40–0.90F, (20°–40°)=0.25–0.60F, (40°–50°)=0.10–0.40, F(50°–60°)=0.05–0.25 and F(>60°)=0.00 and where further, for any two ranges $\alpha'_s$ and $\alpha'_t$, $F(\alpha'_s) > F(\alpha'_t)$ in case $\alpha'_t$ is more peripheric than $\alpha'_s$.

7. An apparatus according to claim 3, in which each annular zone (21–25) of the absorption filter (18) displays uniform absorbance.

8. An apparatus according to claim 4, in which at least one annular zone (31–35) of the absorption filter (18) displays at least one subzone of uniform maximum absorbance $ABS_{max}$ (31a–34a) and at least one subzone of no absorbance (32b–35b).

9. An apparatus according to claim 1, in which the detector (19) has a detector angular sensitivity defining a detector angular absorbance $DAA(\alpha)$ at a scattering angle $\alpha$ and in which the sample has an effective optical pathlength defining a pathlength angular absorbance $PAA(\alpha)$ at the scattering angle $\alpha$, in which the absorption filter (18) has an absorbance described by any mathematical function $G(\alpha) = ABS_{max} - (DAA(\alpha) + PAA(\alpha))$, where $ABS_{max}$ is the maximum absorbance of the absorption filter.

10. An apparatus according to claim 1, in which the absorption filter (18) consists of a foil of polymer material onto which a light absorbing chemical compound has been deposited.

11. An apparatus for optical measurements on light scattering samples comprising at least one light emission means (12), a sample cuvette (15) with a sample chamber and a detecting means (19), the apparatus further being characterised in that it comprises
an interference filter which is positioned in the light path between the sample cuvette (15) and the detecting means (19), and which is selected from the groups of band pass filters and long wavelength pass filters having a center wavelength and a cut-off wavelength, respectively, which are longer than the wavelength of the light from the light emission means.

12. An apparatus according to claim 11 for optical measurements of the concentration of any of hemoglobin, oxyhemoglobin, deoxyhemoglobin, methemoglobin, carboxyhemoglobin, sulfhemoglobin, bilirubin and/or diagnostic dyes.

13. An apparatus according to claim 11, in which the interference filter is a band pass filter of a center wavelength in the range 505–630 nm, or is a long wavelength pass filter of a cut-off wavelength in the range 505–630 nm.

14. An apparatus according to claim 1, in which the filter is provided as a separate component.

15. An apparatus according to claim 1, in which the filter is provided as an integrated part of the sample cuvette (15) or an integrated part of the detector (19).

16. An apparatus according to claim 15 in which the sample cuvette (15) has a light exit window (16) and in which the filter is printed onto the light exit window (16).

17. An apparatus according to claim 15, in which the filter is provided as an integrated part of the sample cuvette (15) and where the sample cuvette (15) with the filter is a disposable unit for use in one or a few measurements only.

18. An apparatus according to claim 1, in which the detecting means (19) has a detection range, defined by the scattering angle $\alpha$, of at least 0–50°.

19. An apparatus according to claim 1, in which the distance between the center of the sample chamber and the detecting means (19) is in the range 0.2–1.5 millimeter.

20. An apparatus according to claim 1, in which the detecting area of the detecting means (19) is at least 25 square millimeter.

21. An apparatus according to claim 1, in which the apparatus comprises one or more optical couplings, which are positioned between the sample cuvette (15) and the filter (18) and/or between the filter (18) and the detecting means (19).

22. An apparatus according to claim 21, in which the thickness of the one or more optical couplings is in the range 1–100 μm.

23. An apparatus according to claim 21, in which the one or more optical couplings are made of glycerols, silicones or acrylates.

24. An apparatus according to claim 1, in which an aperture is placed between the light source (12) and the sample cuvette (15).

25. An apparatus according to claim 24, in which the aperture has an area not larger than 1 square millimeter.

26. A sample cuvette (15) for optical measurements on light scattering samples comprising a sample chamber and light entry and light exit windows (16), respectively, on the walls defining the sample chamber, the sample cuvette being characterised in that it comprises
an absorption filter (18) as an integrated part of the sample cuvette (15), positioned on or into the exit window (16) of the sample cuvette (15), said absorption filter (18) has a center and a periphery and an absorbance which decreases from the center towards the periphery.

27. A sample cuvette (15) according to claim 26, in which the absorption filter (18) has annular zones (21–25) defined by a range of scattering angles $\alpha'_n$, each zone having an absorbance $F(\alpha'_n)$, so that for any two annular zones of the absorption filter (18), defined by the ranges of scattering angles $\alpha'_s$ and $\alpha'_t$, the corresponding absorbances being $F(\alpha'_s)$ and $F(\alpha'_t)$, $F(\alpha'_s) > F(\alpha'_t)$ in case $\alpha'_t$ is more peripheral than $\alpha'_s$.

28. A sample cuvette according to claim 26, in which the absorption filter (18) has an absorbance in the scattering angle ranges 0°–20°, 20°–40°, 40°–50°, 50°–60° and >60°, respectively, of $F(0°–20°) = 0.40–0.90$, $F(20°–40°) = 0.25–0.60$, $F(40°–50°) = 0.10–0.40$, $F(50°–60°) = 0.05–0.25$ and $F(>60°) = 0.00$ and where further, for any two ranges $\alpha'_s$ and $\alpha'_t$, $F(\alpha'_s) > F(\alpha'_t)$ in case $\alpha'_t$ is more peripheral than $\alpha'_s$.

29. A sample cuvette (15) according to claim 27, in which each annular zone (21–25) of the absorption filter (18) displays uniform absorbance.

30. A sample cuvette (15) according to claim 27, in which at feast one annular zone (31–35) of the absorption filter (18) displays at least one subzone of uniform maximum absorbance $ABS_{max}$ (31*a*–34*a*) and at least one subzone of no absorbance (32*b*–35*b*).

31. A sample cuvette (15) according to claim 26, in which the absorption filter (18) consists of a foil of polymer material onto which a light absorbing chemical compound has been deposited.

32. A sample cuvette (15) for optical measurements on light scattering samples comprising a sample chamber and light entry and light exit windows (16), respectively, on the walls defining the sample chamber, the sample cuvette being characterised in that it comprises an interference filter as an integrated part of the sample cuvette (15), positioned on or into the exit window (16) of the sample cuvette (15) and which is selected from the groups of band pass filters and long wavelength pass filters.

33. A sample cuvette (15) according to claim 32, in which the interference filter is a band pass filter of a center wavelength in the range 505–630 nm, or is a long wavelength pass filter of a cut-off wavelength in the range 505–630 nm.

34. A sample cuvette (15) according to claim 26, in which the filter is printed onto the light exit window (16) of the sample cuvette (15).

35. A sample cuvette (15) according to claim 26, in which the sample cuvette (15) is a disposable unit for use in one or a few measurements only.

36. A method for optical measurements on light scattering samples, in which (1) light of one or more wavelengths from at least one light emission means (12) is passed through the sample, and (2) scattered light is detected by a detecting means (19), which method employs an apparatus comprising at least one light emission means (12), a sample cuvette (15) with a sample chamber, the dectecting means (19), and an absorption filter (18) which is positioned in the light path between the sample cuvette (15) and the detecting means (19), said absorption filter (18) having a center and a periphery and an absorbance which decreases from the center towards the periphery.

37. A method for optical measurements according to claim 36, in which light of only one wavelength is used.

38. A method for optical measurements according to claim 36, in which light of at least 2 wavelengths is used.

39. A method for optical measurements according to claim 36 for the determination of the concentration of any hemoglobin, oxyhemoglobin, deoxyhemoglobin, methemoglobin, carboxyhemoglobin sulfhemoglobin, bilirubin and/or diagnostic dyes.

40. A method for optical measurements according to claim 36, in which measurements are preformed on non-flowing samples situated in the sample chamber.

* * * * *